(12) United States Patent
Muhamed et al.

(10) Patent No.: US 11,786,477 B2
(45) Date of Patent: Oct. 17, 2023

(54) FIBRIN PARTICLES AND METHODS OF MAKING THE SAME

(71) Applicant: NORTH CAROLINA STATE UNIVERSITY, Raleigh, NC (US)

(72) Inventors: Ismaeel Muhamed, Raleigh, NC (US); Ashley C. Brown, Raleigh, NC (US); Frances S. Ligler, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 16/768,760

(22) PCT Filed: Dec. 3, 2018

(86) PCT No.: PCT/US2018/063619
§ 371 (c)(1),
(2) Date: Jun. 1, 2020

(87) PCT Pub. No.: WO2019/109079
PCT Pub. Date: Jun. 6, 2019

(65) Prior Publication Data
US 2021/0169813 A1 Jun. 10, 2021

Related U.S. Application Data

(60) Provisional application No. 62/593,556, filed on Dec. 1, 2017.

(51) Int. Cl.
*A61K 9/50* (2006.01)
*A61P 17/02* (2006.01)
*A61K 47/69* (2017.01)
*A61K 45/06* (2006.01)

(52) U.S. Cl.
CPC .......... *A61K 9/5052* (2013.01); *A61K 9/5089* (2013.01); *A61K 45/06* (2013.01); *A61K 47/6925* (2017.08); *A61P 17/02* (2018.01)

(58) Field of Classification Search
None
See application file for complete search history.

(56) References Cited

U.S. PATENT DOCUMENTS

| | | |
|---|---|---|
| 4,270,537 A | 6/1981 | Romaine |
| 4,596,556 A | 6/1986 | Morrow et al. |
| 4,790,824 A | 12/1988 | Morrow et al. |
| 4,886,499 A | 12/1989 | Cirelli et al. |
| 4,940,460 A | 7/1990 | Casey et al. |
| 4,941,880 A | 7/1990 | Burns |
| 5,015,235 A | 5/1991 | Crossman |
| 5,064,413 A | 11/1991 | McKinnon et al. |
| 5,141,496 A | 8/1992 | Dalto |
| 5,190,521 A | 3/1993 | Hubbard et al. |
| 5,312,335 A | 5/1994 | McKinnon et al. |
| 5,328,483 A | 7/1994 | Jacoby |
| 5,334,144 A | 8/1994 | Alchas |
| 5,339,163 A | 8/1994 | Homma et al. |
| 5,383,851 A | 1/1995 | McKinnon, Jr. et al. |
| 5,417,662 A | 5/1995 | Hjertman et al. |
| 5,466,220 A | 11/1995 | Brenneman |
| 5,480,381 A | 1/1996 | Weston |
| 5,503,627 A | 4/1996 | McKinnon |
| 5,520,639 A | 5/1996 | Peterson et al. |
| 5,527,288 A | 6/1996 | Gross et al. |
| 5,569,189 A | 10/1996 | Parsons |
| 5,599,302 A | 2/1997 | Lilley et al. |
| 5,649,912 A | 7/1997 | Peterson |
| 5,704,911 A | 1/1998 | Parsons |
| 5,893,397 A | 4/1999 | Peterson |
| 5,993,412 A | 11/1999 | Deily et al. |
| 6,150,505 A | 11/2000 | Marx et al. |
| 6,552,172 B2 | 4/2003 | Marx et al. |
| 6,599,515 B1 | 7/2003 | Delmotte |
| 2003/0045690 A1* | 3/2003 | Marx ............... B82Y 5/00 435/68.1 |
| 2003/0166867 A1 | 9/2003 | Marx et al. |
| 2016/0271292 A1 | 9/2016 | Barker et al. |

FOREIGN PATENT DOCUMENTS

| | | |
|---|---|---|
| EP | 3165240 | 10/2017 |
| WO | 97/13537 | 4/1997 |
| WO | 97/37705 | 10/1997 |
| WO | 99/34850 | 7/1999 |

OTHER PUBLICATIONS

Geer DJ, Swartz DD, Andreadis ST. Biomimetic delivery of keratinocyte growth factor upon cellular demand for accelerated wound healing in vitro and in vivo. The American journal of pathology. Dec. 1, 2005;167(6):1575-86. (Year: 2005).*
Vedakumari WS, Prabu P, Babu SC, Sastry TP. Fibrin nanoparticles as Possible vehicles for drug delivery. Biochimica et Biophysica Acta (BBA)—General Subjects. Aug. 1, 2013;1830(8):4244-53. (Year: 2013).*
Ahmad E, Fatima MT, Hoque M, Owais M, Saleemuddin M. Fibrin matrices: The versatile therapeutic delivery systems. International journal of biological macromolecules. Nov. 1, 2015;81:121-36. (Year: 2015).*
Gaumet M, Vargas A, Gurny R, Delie F. Nanoparticles for drug delivery: the need for precision in reporting particle size parameters. European journal of pharmaceutics and biopharmaceutics. May 1, 2008;69(1):1-9. (Year: 2008).*
Scheraga HA. The thrombin-fibrinogen interaction. Biophysical chemistry. Dec. 20, 2004;112(2-3):117-30. (Year: 2004).*
Amo, Laura, et al. "Involvement of Platelet-Tumor Cell Interaction in Immune Evasion. Potential Role of Podocalyxin-Like Protein 1." Frontiers in oncology 4 (2014): 245.

(Continued)

*Primary Examiner* — Nissa M Westerberg
(74) *Attorney, Agent, or Firm* — Meunier Carlin & Curfman LLC

(57) ABSTRACT

Disclosed herein are low density particles comprising polymerized fibrin that are micrometer or nanometer sized in diameter. The particles can further include at least one therapeutic agent. The particles may be used to treat wounds, by administration directly or systemically to the site of the wound. Exemplary wounds that may be treated with the fibrin particles include a trauma wound, a surgical wound, a burn wound, or an ulcer wound. Also disclosed herein are methods for preparing the particles using a shearing process.

13 Claims, 6 Drawing Sheets

(56) References Cited

OTHER PUBLICATIONS

Arai, Mary, Takashi Matsuzaki, and Setsunosuke Ihara. "Wound closure on the neonatal rat skin I. The modulation of the thickness of epidermis at the closing incisional wounds." CellBio 2.04 (2013): 248.

Barry, Adrienne K., et al. "α-catenin cytomechanics—role in cadherin-dependent adhesion and mechanotransduction." Journal of cell science 127.8 (2014): 1779-1791.

Bellis, Susan L. "Advantages of RGD peptides for directing cell association with biomaterials." Biomaterials 32.18 (2011): 4205-4210.

Branski, Ludwik K., et al. "A review of gene and stem cell therapy in cutaneous wound healing." Burns 35.2 (2009): 171-180.

Brittberg, Mats, et al. "Influence of fibrin sealant (Tisseel®) on osteochondral defect repair in the rabbit knee." Biomaterials 18.3 (1997): 235-242.

Brown, Ashley C., and Thomas H. Barker. "Fibrin-based biomaterials: modulation of macroscopic properties through rational design at the molecular level." Acta biomaterialia 10.4 (2014): 1502-1514.

Butler, James P., et al. "Traction fields, moments, and strain energy that cells exert on their surroundings." American Journal of Physiology—Cell Physiology 282.3 (2002): C595-C605.

Chapin, John C., and Katherine A. Hajjar. "Fibrinolysis and the control of blood coagulation." Blood reviews 29.1 (2015): 17-24.

Chen, Zhuo J., et al. "A novel three-dimensional wound healing model." Journal of Developmental Biology 2.4 (2014): 198-209.

Chester, Daniel, and Ashley C. Brown. "The role of biophysical properties of provisional matrix proteins in wound repair." Matrix Biology 60 (2017): 124-140.

Clark, R. A. "Fibrin and wound repair." Ann NY Acad Sci 936 (2001): 355-367.

Cukjati, David, Stanislav Reberšek, and Damijan Miklavčič. "A reliable method of determining wound healing rate." Medical and Biological Engineering and Computing 39.2 (2001): 263-271.

Drury, R. A. B. "Theory and practice of histological techniques." Journal of Clinical Pathology 36.5 (1983): 609.

Dunn, Louise, et al. "Murine model of wound healing." JoVE (Journal of Visualized Experiments) 75 (2013): e50265.

Dutta, Sulagna, and Pallav Sengupta. "Men and mice: relating their ages." Life sciences 152 (2016): 244-248.

Evans, Heather M., et al. "In situ formation, manipulation, and imaging of droplet-encapsulated fibrin networks." Lab on a Chip 9.13 (2009): 1933-1941.

Ferguson, James, Sylvia Nürnberger, and Heinz Redl. "Fibrin: the very first biomimetic glue—still a great tool." Biological adhesive systems. Springer, Vienna, 2010. 225-236.

Fife, Caroline E., et al. "Wound care outcomes and associated cost among patients treated in US outpatient wound centers: data from the US Wound Registry." Wounds 24.1 (2012): 10.

Finch, Paul W., and Jeffrey S. Rubin. "Keratinocyte growth factor/fibroblast growth factor 7, a homeostatic factor with therapeutic potential for epithelial protection and repair." Advances in cancer research 91 (2004): 69.

Frank, Stefan, Barbara Munz, and Sabine Werner. "The human homologue of a bovine non-selenium glutathione peroxidase is a novel keratinocyte growth factor-regulated gene." Oncogene 14.8 (1997): 915-921.

Friedlaender, Gary E., et al. "The role of recombinant human platelet-derived growth factor-BB (rhPDGF-BB) in orthopaedic bone repair and regeneration." Current pharmaceutical design 19.19 (2013): 3384-3390.

Gao, Xiaohu, et al. "In vivo molecular and cellular imaging with quantum dots." Current opinion in biotechnology 16.1 (2005): 63-72.

Guo, Wenjun, and Filippo G. Giancotti. "Integrin signalling during tumour progression." Nature reviews Molecular cell biology 5.10 (2004): 816-826.

Hanson, Angela J., and Mark T. Quinn. "Effect of fibrin sealant composition on human neutrophil chemotaxis." Journal of Biomedical Materials Research: An Official Journal of The Society for Biomaterials, The Japanese Society for Biomaterials, and The Australian Society for Biomaterials and the Korean Society for Biomaterials 61.3 (2002): 474-481.

Redl, H., and G. Schlag. "Fibrin sealant and its modes of application." Fibrin sealant in operative medicine. Springer, Berlin, Heidelberg, 1986. 13-26.

Hickerson, William L., Israel Nur, and Roberto Meidler. "A comparison of the mechanical, kinetic, and biochemical properties of fibrin clots formed with two different fibrin sealants." Blood coagulation & fibrinolysis 22.1 (2011): 19-23.

Ho Hsio-O, "Fibrin-Based Drug Delivery Systems. II." The Preparation and Characterization of Microbeads, 20:4, 1994, 535-546.

Ho, Wendy, et al. "The behavior of human mesenchymal stem cells in 3D fibrin clots: dependence on fibrinogen concentration and clot structure." Tissue Engineering 12.6 (2006): 1587-1595.

Kepivance™ (palifermin) Initial U.S. Approval: 2004 https://www.accessdata.fda.gov/drugsatfda_docs/label/2004/125103lbl.pdf.

Kaplan, Zane S., et al. "Thrombin-dependent intravascular leukocyte trafficking regulated by fibrin and the platelet receptors GPIb and PAR4." Nature communications 6.1 (2015), 7835.

Kim, Tae-Jin, et al. "Dynamic visualization of α-catenin reveals rapid, reversible conformation switching between tension states." Current biology 25.2 (2015): 218-224.

Koria, Piyush, et al. "Self-assembling elastin-like peptides growth factor chimeric nanoparticles for the treatment of chronic wounds." Proceedings of the National Academy of Sciences 108.3 (2011): 1034-1039.

Lanir, N.; Ciano, P. S.; Van de Water, L.; McDonagh, J.; Dvorak, A. M.; Dvorak, H. F. "Macrophage Migration in Fibrin Gel Matrices. II. Effects of Clotting Factor XIII, Fibronectin, and Glycosaminoglycan Content on Cell Migration." J. Immunol. 1988, 140 (7), 2340-2349.

Larson, Michael J., et al. "Efficacy of a fibrin hemostatic bandage in controlling hemorrhage from experimental arterial injuries." Archives of Surgery 130.4 (1995): 420-422.

Lendrum, A. C., et al. "Studies on the character and staining of fibrin." Journal of clinical pathology 15.5 (1962): 401.

Lin, Audrey, Akishige Hokugo, and Ichiro Nishimura. "Wound closure and wound management: A new therapeutic molecular target." Cell adhesion & migration 4.3 (2010): 396-399.

Maksym, Geoffrey N., et al. "Mechanical properties of cultured human airway smooth muscle cells from 0.05 to 0.4 Hz." Journal of Applied Physiology 89.4 (2000): 1619-1632.

McClain, Steven A., et al. "Mesenchymal cell activation is the rate-limiting step of granulation tissue induction." The American journal of pathology 149.4 (1996): 1257-1270.

Muhamed et al., "90 Engineering Fibrin Nanoparticles for Enhanced Wound Healing", accessed Nov. 28, 2017.

Muhamed, Ismaeel, Farhan Chowdhury, and Venkat Maruthamuthu. "Biophysical tools to study cellular mechanotransduction." Bioengineering 4.1 (2017): 12.

Muhamed, Ismaeel, et al. "E-cadherin-mediated force transduction signals regulate global cell mechanics." Journal of cell science 129.9 (2016): 1843-1854.

Nürnberger, Sylvia, et al. "Properties and potential alternative applications of fibrin glue." Biological adhesive systems. Springer, Vienna, 2010. 237-259.

Ozdemir, Tugba, et al. "Fibrin serves as a divalent ligand that regulates neutrophil-mediated melanoma cells adhesion to endothelium under shear conditions." American Journal of Physiology—Cell Physiology 302.8 (2012): C1189-C1201.

Pollock, P. J.; Schumacher, J. In Equine Medicine, Surgery and Reproduction; Elsevier, 2012; pp. 469-487.

Radtke, Michelle L., and Jill M. Kolesar. "Palifermin (Kepivance™) for the treatment of oral mucositis in patients with hematologic malignancies requiring hematopoietic stem cell support." Journal of Oncology Pharmacy Practice 11.3 (2005): 121-125.

Rubin, Jeffrey S. "Recent developments in palifermin basic, preclinical and clinical research." Journal of cellular and molecular medicine 17.9 (2013): 1063.

(56) References Cited

OTHER PUBLICATIONS

Rubin, Jeffrey S., et al. "Keratinocyte growth factor." Cell biology international 19.5 (1995): 399-412.
Schlag, G.; Redl, H.; Turnher, M.; Dinges, H. P. "In Fibrin Sealant in Operative Medicine"; Springer Berlin Heidelberg: Berlin, Heidelberg, 1986; pp. 3-12.
Seemann, Ralf, et al. "Droplet based microfluidics." Reports on progress in physics 75.1 (2011): 016601.
Senderoff, "Journal of parenteral science and technology: a publication of the Parenteral Drug Association", J. Parenteral Sci. & Tech. (1991) 45(1):2-6.
Singer, Adam J., and Richard AF Clark. "Cutaneous wound healing." New England journal of medicine 341.10 (1999): 738-746.
Sproul, E.; Nandi, S.; Brown, A. "In Peptides and Proteins as Biomaterials for Tissue Regeneration and Repair", Elsevier, 2018; pp. 151-173.
Tabeling, P. "A brief introduction to slippage, droplets and mixing in microfluidic systems." Lab on a Chip 9.17 (2009): 2428-2436.
Takeichi, M.; Nakagawa, S. Curr. Protoc. Cell Biol. 2001, Chapter 9, Unit 9.3.
Tang, Xin, et al. "A novel cell traction force microscopy to study multi-cellular system." PLoS Comput Biol 10.6 (2014): e1003631.
Tse, Justin R, and Adam J Engler. 2010. "Preparation of Hydrogel Substrates with Tunable Mechanical Properties." Current Protocols in Cell Biology / Editorial Board, Juan S. Bonifacino . . . [ et al.] Chapter 10 (Jun.): Unit 10.16. doi:10.1002/0471143030.cb1016s47.
Undas, Anetta, and Robert AS Ariëns. "Fibrin clot structure and function: a role in the pathophysiology of arterial and venous thromboembolic diseases." Arteriosclerosis, thrombosis, and vascular biology 31.12 (2011): e88-e99.
Wang, Ning, et al. "Cell prestress. I. Stiffness and prestress are closely associated in adherent contractile cells." American Journal of Physiology—Cell Physiology 282.3 (2002): C606-C616.
Xu, Jiahua, and R. A. Clark. "Extracellular matrix alters PDGF regulation of fibroblast integrins." The Journal of cell biology 132.1 (1996): 239-249.
Yakovlev, S., et al. "Interaction of fibrin with VE-cadherin and anti-inflammatory effect of fibrin-derived fragments." Journal of Thrombosis and Haemostasis 9.9 (2011): 1847-1855.
Yeung, A. M., et al. "Fibrin glue inhibits migration of ocular surface epithelial cells." Eye 30.10 (2016): 1389-1394.
International Preliminary Report on Patentability issued for Application No. PCT/US2018/063619, dated Jun. 11, 2020.
International Search Report and Written Opinion issued in corresponding application No. PCT/US2018/063619, dated Feb. 15, 2019, 9 pages.
Evans, et al. "In situ formation, manipulation, and imaging of droplet-encapsulated fibrin networks." Lab on a Chip 9 13 (Mar. 30, 2009): 1933-1941.
Seemann, et al. "Droplet based microfluidics." Reports on progress in physics 75.1 (Dec. 22, 2011): 016601, p. 28 Section 7.2.2.
Muhamed, et al. "Fibrin nanoparticles coupled with keratinocyte growth factor enhance dermal 1-3, wound healing rate." ACS applied materials & interfaces (Jan. 3, 2019).
Souri et al. "The Non-catalytic B Subunit of Coagulation Factor XIII Accelerates Fibrin Cross-linking." The Journal of Biological Chemistry, vol. 290, No. 19, 12027-12029. May 8, 2015.

* cited by examiner

FIBRIN PARTICLES AND METHODS OF MAKING THE SAME

CROSS-REFERENCE TO RELATED APPLICATION

This is a national stage application filed under 35 U.S.C. § 371 of PCT/US2018/063619 filed on Dec. 3, 2018, and entitled "Fibrin Particles and Methods of Making the Same," which claims the benefit of U.S. Provisional Application 62/593,556, filed on Dec. 1, 2017, the contents of which are hereby incorporated in their entireties.

FIELD OF THE INVENTION

The invention is directed to low density, flowable fibrin particles, the use of such particles to deliver therapeutic agents to targeted tissues to treat wounds and other tissue injuries, as well as methods of preparing low density fibrin particles using shearing processes.

BACKGROUND

Fibrin is a naturally occurring non-globular protein involved in the clotting of blood. Briefly, after a blood vessel is damaged, platelets aggregate around the wound. Platelets generate active thrombin on their cell surfaces. Thrombin catalyzes the conversion of soluble fibrinogen into fibrin, which is polymerized primarily through noncovalent interactions. Finally, factor XIII covalently crosslinks the polymerized fibrin to produce a clot. The inability of a wound to heal quickly is a key concern in managing major injuries, especially in patients with impaired coagulation abilities, such as hemophiliacs, diabetics, and sufferers of Von Willebrand disease. Commercially available fibrin sealants have been developed that are composed of bulk fibrin hydrogels polymerized at high density.

In order for current fibrin sealants to achieve suitable polymerization kinetics and mechanics for clinical use, they must be employed at supraphysiological concentrations relative to normally occurring thrombin and fibrinogen concentrations. These fibrin-based wound healing materials are usually formed in situ into a bulk phase dressing during clinical administration. The heavily crosslinked, dense networks can inhibit wound repair due to inhibition of cell migration into the wound. A few fibrin-based particles have been developed for clinical use; these particles are polymerized prior to administration. However, the polymerization process uses elevated temperatures, intensive crosslinking, and densities significantly higher than are physiologically optimum. Among other concerns, the use of elevated temperatures during the crosslinking process can denature a portion of the fibrin proteins, thereby reducing the overall healing efficacy of the particle.

There remains a need for fibrin-based wound healing materials with improved clinical utility and ease of administration. Highly porous fibrin particles could expedite wound healing in a manner similar to natural fibrin formations by enhancing recruitment of appropriate cells and/or by seeding the formation of protective extracellular layers. There remains a need for improved processes for preparing fibrin particles that do not rely on elevated temperatures, factor XIII, or exogenous crosslinkers. There remains a need for fibrin particles with improved storability and easier application to wounds relative to fibrin film-based products.

SUMMARY

It is an object of the invention to create fibrin particles that have physical properties (e.g. crosslinking density) similar to naturally occurring fibrin-based formations or clots. Another object of the invention is to create such particles at low temperatures that do not denature the fibrin molecules. Another object of the invention is to create fibrin particles that can also act as carriers for therapeutic agents that enhance wound repair. Another object of the invention is to create fibrin-based wound repair materials that can be easily applied to a wound (e.g. flowable particles). Another object of the invention is to include the particles in a carrier that facilities therapeutic use.

Disclosed herein are low density particles comprising polymerized fibrin. The particles can further include at least one therapeutic agent. The particles may be used to treat wounds, for instance by administering the particles to the site of the wound. Exemplary wounds that may be treated with the particles include, but are not limited to, a trauma wound, a surgical wound, a burn wound, or an ulcer wound.

Also disclosed herein are methods for preparing the particles disclosed above. Generally speaking, the particles can be prepared by applying a shear stress to an aqueous composition including polymerized fibrin. In some embodiments, the shear stress can be achieved using a microfluidic device capable of combining two fluid streams. The first fluid stream includes a dispersive phase, which is the aqueous phase containing the fibrin polymer, which can be obtained by combining fibrinogen and thrombin. In some embodiments, small amounts of Factor XIII may also be present in the starting materials; however, the dispersive phase does not include externally added factor XIII or other non-biologically derived agents capable of crosslinking the fibrin molecules. The second fluid stream includes a continuous phase, which is generally a water-immiscible fluid. The first fluid stream contained in the "dispersive channel" is injected into the second fluid stream contained in the "continuous channel", thereby forming particles of polymerized fibrin dispersed in the continuous phase. The particles created by the shearing of the polymer at the intersection of the two streams can be collected from the outlet of the continuous channel and separated from the continuous phase. Additional therapeutic agents can be included in the particles during fibrin polymerization or subsequently added to the formed particles. Such therapeutic agents can be entrapped within or covalently attached to the particles.

The details of one or more embodiments are set forth in the descriptions below. Other features, objects, and advantages will be apparent from the description and from the claims.

DETAILED DESCRIPTION

Figure 1:
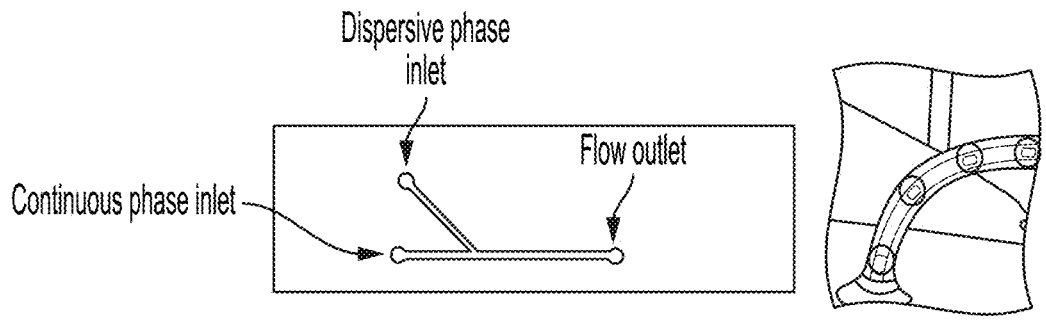
FIG. 1 includes a schematic of an exemplary microfluidic device.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

As used herein, the phrase "therapeutic agent" refers to any agent that, when administered to a subject, has a therapeutic and/or diagnostic effect and/or elicits a desired biological and/or pharmacological effect.

Disclosed herein are particles comprising polymerized fibrin. The particles have diameters in the nanometer to micrometer range. In some instances, the lyophilized particles have a density no greater than 100 mg/ml, no greater than 50 mg/ml, no greater than about 25 mg/ml, no greater than about 10 mg/ml, no greater than about 5 mg/ml, no greater than about 2.5 mg/ml, no greater than about 1.0 mg/ml, no greater than about 0.5 mg/ml, or no greater than about 0.1 mg/ml. In some instances, the particles can have a density between about 0.1-25 mg/ml between about 0.1-10 mg/ml, between about 0.1-5 mg/ml, between about 0.1-1.0 mg/ml, between 1-10 mg/ml, or between about 1-5 mg/ml. In some instances, the particles can have a density from 0.1-100 mg/ml, from 0.1-50 mg/ml, from 0.1-25 mg/ml, from 0.1-10 mg/ml, from 0.1-5 mg/ml, from 0.5-10 mg/ml, or from 0.5-5 mg/ml.

In some embodiments, the hydrated particles can have an average particle size no greater than about 10,000 nm, no greater than about 5,000 nm, no greater than about 2,500 nm, no greater than about 1,000 nm, no greater than about 750 nm, no greater than about 500 nm, or no greater than about 250 nm. In some embodiments, the particles can have an average particle size between about 100-10,000 nm, between about 100-5,000 nm, between about 100-2,500 nm, between about 250-2,500 nm, between about 500-2,500 nm, between about 1,000-2,500 nm, between about 100-1,500 nm, between about 100-1,000 nm, between about 100-750 nm, between about 100-500 nm, or between 100-250 nm. In yet further embodiments, the inventive particles can have an average particle size no greater than 500 μm, no greater than 250 μm, no greater than 100 μm, no greater than 75 μm, no greater than 50 μm, no greater than 25 μm, no greater than 10 μm, no greater than 5 μm, no greater than 1 μm, no greater than 0.75 μm, no greater than 0.5 μm, no greater than 0.25 μm, no greater than 0.1 μm, no greater than 0.05 μm, no greater than 0.025 μm, or no greater than 0.01 μm. In certain embodiments, the particles can have an average particle size from 0.01-100 μm, from 0.025-100 μm, from 0.05-100 μm, from 0.1-100 μm, from 0.25-100 μm, from 0.50-100 μm, from 0.75-100 μm, from 1-100 μm, from 5-100 μm, from 10-100 μm, from 25-100 μm, from 50-100 μm, from 0.01-50 μm, from 0.01-25 μm, from 0.01-10 μm, from 0.01-5 μm, from 0.01-2.5 μm, from 0.01-1 μm, from 0.01-0.75 μm, from 0.01-0.5 μm, from 0.01-0.25 μm, from 0.01-0.1 μm, from 0.05-1 μm, from 0.075-1 μm, from 0.1-1 μm, from 0.25-1 μm, from 0.5-1 μm, from 50-500 μm, from 100-500 μm, from 250-500 μm.

The average particle size in hydrated form was measured using dynamic light scattering (DLS). The dehydrated size was measured by drying particles on glass and measuring sizes using an atomic force microscopy (air topography mode); the sizes of the particles are smaller after dehydration.

The fibrin particles disclosed herein are porous and have hydrogel properties. For instance, dehydrated particles have a substantially flat shape, but when suspended in water attain a bulbous, more spherical shape. For instance, when dehydrated, the particles may have a height that is no more than 20%, no more than 15%, no more than 10%, no more than 8%, no more than 6%, no more than 4%, or no more than 2% of the width.

In some embodiments, the fibrin particles do not exhibit a substantial degree of covalent crosslinking. For instance, the particles may have a degree of covalent crosslinking no greater than 25%, no greater than 20%, no greater than 15%, no greater than 10%, no greater than 5%, no greater than 2.5%, no greater than 1%, or no greater than 0.5%. Crosslinking may be evaluated using the techniques disclosed in U.S. Pat. No. 6,150,505, e.g., col. 3, line 41-55, and col. 9, line 52-col 10, line 11, incorporated herein by reference.

The particles described in each of the aforementioned paragraphs can further include at least one therapeutic agent. Exemplary therapeutic compounds include antimicrobials, analgesics and anti-inflammatories, as well as combinations thereof. In some cases, the therapeutic compound is an antimicrobial agent, e.g., an agent that inhibits the growth of or kill microbes such as bacteria, mycobacteria, viruses, fungi, and parasites. Anti-microbial agents therefore include anti-bacterial agents, anti-mycobacterial agents, anti-viral agents, anti-fungal agents, and anti-parasite agents. Suitable antimicrobials include antibiotics, antimicrobial peptides and metallic compounds.

Suitable antibiotics include penicillins, cephalosporins, quinolones (including fluoroquinolones), aminoglycosides, monobactams, carbapenems, tetracyclines, macrolides, peptides, and others. In some embodiments, the antibiotics is one or more compounds selected from streptomycin, neomycin, kanamycin, amikacin, gentamycin, tobramycin, sisomicin, arbekacin, apramycin, netilmicin, paromomycin, spectinomycin, ciprofloxacin, levofloxacin, lomefloxacin, moxifloxacin, norfloxacin, ofloxacin, sparfloxacin, trvafloxacin, gatifloxacin, gemifloxacin, cinoxacin, nalidixic acid, azithromycin, clarithromycin, dirithromycin, erythromycin, roxithromycin, troleandomycin, telithromycin, spectinomycin, indolicidin, defen sin, cecropin, magainin, yancomycin, teicoplanin, telavancin, ramoplanin, decaplanin, bleomycin, colistin (polymyxin E), colistin A (polymyxin E1), colistin B (polymyxin E2), colistin sulfate, colistimethate sodium, actinomycin, bacitracin, polymyxin B, gentamicin, gentamicin sulfate, neomycin, kanamycin, tobramycin, metronidazole, clotrimazole, secnidazole, omidazole, imidazole, linezolid, doxycycline, tetracycline, oxytetracycline, chlortetracycline, demeclocycline, lymecycline, meclocycline, methacycline, minocycline, rolitetracycline, and tigecycline.

Suitable analgesics include opioids, capsaicin, diclofenac, lidocaine, benzocaine, methyl salicylate, trolamine, prilocaine, pramoxine, dibucaine, phenol, tetracaine, camphor, dyclonine, and menthol. Suitable anti-inflammatories include alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, and zomepirac sodium.

In some cases, the therapeutic agent can include at least one growth factor, cytokine, ehemokine, cluster differentiation (CD) antigen, neutrophin, hormone, enzyme, viral antigen, bacterial antigen, recombinant protein, natural protein, monoclonal antibody, polyclonal antibody, donor blood serum protein, donor blood plasma protein, or small molecule drug. Exemplary growth factors include keratinocyte growth factor (KGF), platelet derived growth factor (PDGF), transforming growth factor-beta (TGF$_\beta$), interleukin, activin, colony stimulating factor, connective tissue growth factor (CTGF), epidermal growth factor (EGF), Epigen, erythropoietin, fibroblast growth factor (FGF), galectin, hepatoma-derived growth factor (HDGF), hepatocyte growth factor, insulin-like growth factor binding protein (IGFBP), insulin-like growth factor, insulin, leptin, macrophage migration inhibitory factor, melanoma inhibitory factor, myostatin, noggin, nephroblastoma, overexpressed (NOV), omentin, oncostatinM, osteopontin, osteoprotogerin (OPG), periostin, placenta growth factor, placental lactogen, prolactin, RANK ligand, retinol binding protein, stem cell factor, transforming growth factor, and vascular endothelial growth factor (VEGF). This includes associated isoforms from these growth factor families. In certain preferred embodiments, the particles described in the above paragraphs can include KGF, interleukin-2 (IE-2), and/or interleukin-6 (IL-6).

The therapeutic agent can also include one or more cell and stem cell recruiting factor, for instance cell recruiting proteins, peptides, oligonucleotides, and small molecules. Exemplary cell recruiting factors include KGF, CTGF, FGF, insulin-like growth factor, VEGF, EGF, TGFβ, PDGF, G-CSF, GM-CSF, macrophage inflammatory protein-1 α and β, and erythropoietin.

Therapeutic agents, such as described above, can be covalently conjugated to the fibrin molecules in the particle. For instance, the therapeutic agent can be conjugated to the surface of the particle, or can be conjugated throughout the volume of the particle. In further embodiments, a therapeutic agent can be entrapped or encapsulated within the particle, for instance, not covalently bonded to the fibrin molecules. The therapeutic agent can be homogenously dispersed throughout the particle, either through covalent or non-covalent bonds.

Therapeutic agents may be conjugated to the fibrin molecules through a covalent linker. Any suitable linker can be used in accordance with the present invention. Linkers may be used to form amide linkages, ester linkages, disulfide linkages, etc. Linkers may contain carbon atoms or heteroatoms (e.g., nitrogen, oxygen, sulfur, etc.). Typically, linkers are 1 to 50 atoms long, 1 to 40 atoms long, 1 to 25 atoms long, 1 to 20 atoms long, 1 to 15 atoms long, 1 to 10 atoms long, or 1 to 10 atoms long. Linkers may be substituted with various substituents including, but not limited to, hydrogen atoms, alkyl, alkenyl, alkynyl, amino, alkylamino, dialkylamino, trialkylamino, hydroxyl, alkoxy, halogen, aryl, heterocyclic, aromatic heterocyclic, cyano, amide, carbamoyl, carboxylic acid, ester, thioether, alkylthioether, thiol, and ureido groups. As would be appreciated by one of skill in this art, each of these groups may in turn be substituted.

A simple-to-use linker can be an aliphatic or heteroaliphatic linker. For example, the linker can be a polyalkyl linker. The linker can be a polyether linker. The linker can be a polyethylene linker, such as polyethylene glycol (PEG). The linker can be a short peptide chain, e.g., between 1 and 10 amino acids in length, e.g., 1, 2, 3, 4, or 5 amino acids in length, a nucleic acid, an alkyl chain, etc.

The linker can be a cleavable linker. To give but a few examples, cleavable linkers include protease cleavable peptide linkers, nuclease sensitive nucleic acid linkers, lipase sensitive lipid linkers, glycosidase sensitive carbohydrate linkers, pH sensitive linkers, hypoxia sensitive linkers, photo-cleavable linkers, heat-labile linkers, enzyme cleavable linkers (e.g. esterase cleavable linker), ultrasound-sensitive linkers, x-ray cleavable linkers, etc. In some embodiments, the linker is not a cleavable linker.

Any of a variety of methods can be used to associate a linker with a particle and agent. General strategies include passive adsorption (e.g., via electrostatic interactions), multivalent chelation, covalent bond formation, etc. (Gao et al, 2005, Curr. Op. Biotechnol., 16:63). Click chemistry can be used to associate a linker with an agent (e.g. Diels-Alder reaction, Huigsen 1,3-dipolar cycloaddition, nucleophilic substitution, carbonyl chemistry, epoxidation, dihydroxylation, etc.).

A bifunctional cross-linking reagent can be employed. Such reagents contain two reactive groups, thereby providing a means of covalently associating two target groups. The reactive groups in a chemical cross-linking reagent typically belong to various classes of functional groups such as succinimidyl esters, maleimides, and pyridyldisulfides. Exemplary cross-linking agents include, e.g., carbodiimides, N-hydroxysuccinimidyl-4-azidosalicylic acid (NHS-ASA), dimethyl pimelimidate dihydrochloride (DMP), dimethylsuberimidate (DMS), 3,3'-dithiobispropionimidate (DTBP), N-succinimidyl 3-[2-pyridyldithio]-propionamido (SPDP), succinimidyl α-methylbutanoate, biotinamidohexanoyl-6-amino-hexanoic acid N-hydroxy-succinimide ester (SMCC), succinimidyl-[(N-maleimidopropionamido)-dodecaethyleneglycol]ester (NHS-PEO 12), etc. For example, carbodiimide-mediated amide formation and active ester maleimide-mediated amine and sulfhydryl coupling are widely used approaches.

Common schemes for forming a conjugate involve the coupling of a first functional group on one molecule to a second functional group on a second molecule, sometimes by a two- or three-step reaction sequence. A thiol-containing molecule may be reacted with an amine-containing molecule using a heterobifunctional cross-linking reagent, e.g., a reagent containing both a succinimidyl ester and either a maleimide, a pyridyldisulfide, or an iodoacetamide. Amine-carboxylic acid and thiol-carboxylic acid cross-linking, maleimide-sulfhydryl coupling chemistries (e.g., the maleimidobenzoyl-N-hydroxysuccinimide ester (MBS) method), etc., may be used. Polypeptides can conveniently be attached to particles via amine or thiol groups in lysine or cysteine side chains respectively, or by an N-terminal amino group. Nucleic acids such as RNAs can be synthesized with a terminal amino group. A variety of coupling reagents (e.g., succinimidyl 3-(2-pyridyldithio)propionate (SPDP) and sulfosuccinimidyl-4-(N-maleimidomethyl)cyclohexane-1-carboxylate (sulfo-SMCC) may be used to associate the various components of conjugates. Agents can be prepared with functional groups, e.g., amine or carboxyl groups, available at the surface to facilitate association with a biomolecule. Any biomolecule can be attached to another molecule described herein using any of the methods described herein.

Also disclosed are methods of treating a wound by administering the particles described above to the site the wound. Exemplary wounds that may be treated with the particles include a trauma wound, a surgical wound, a burn wound, or an ulcer wound. Wound patients with coagulation disorders may be advantageously treated with the particles, for instance, diabetics, hemophiliacs, patients with vitamin K deficiency, Von Willebrand disease or other clotting factor deficiencies. The particles can be used to treat wounds in patients undergoing anti-coagulation therapy, for instance patients receiving heparin, fandaparinux, idraparinux, vitamin K, coumadin, direct thrombin inhibitors like argatroban, dabigatran, factor Xa inhibitors like rivaroxaban, apixaban and edoxaban, anti-platelet agents such as clopidogrel and prasugrel. The particles can be used to treat wounds arising from medical procedures such as percutaneous coronary intervention, stent and/or valve placement or repair, transfusion, and dialysis.

The particles described above can be included in a wide variety of pharmaceutical compositions, for instance those including pharmaceutically acceptable carriers. Suitable carriers include water, saline and other liquid formulations, which can be directly administered to a wound site or injected into a patient. In other cases, the particles can be included in a formulation for topical administration, for instance, lotions, sprays, creams, ointments and the like. The compositions can also include a backing layer to secure the composition at a wound site.

The pharmaceutical compositions described herein may be prepared by any method known or hereafter developed in the art of pharmaceutics. In general, such preparatory methods include the step of bringing the active ingredient into association with one or more excipients and/or one or more other accessory ingredients, and then, if necessary and/or desirable, shaping and/or packaging the product into a desired single- or multi-dose unit.

Dosage forms for topical and/or transdermal administration of the particles may include ointments, pastes, creams, lotions, gels, powders, solutions, sprays, inhalants and/or patches. Generally, the active component is admixed under sterile conditions with a pharmaceutically acceptable excipient and/or any needed preservatives and/or buffers as may be required. Additionally, the present invention contemplates the use of transdermal patches, which often have the added advantage of providing controlled delivery of an active ingredient to the body. Such dosage forms may be prepared, for example, by dissolving and/or dispensing the active ingredient in the proper medium. Alternatively or additionally, the rate may be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid compositions to the dermis via a liquid jet injector and/or via a needle which pierces the stratum comeum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient may be as high as the suspension limit of the particles in the liquid phase. Formulations for topical administration may further comprise one or more of the excipients and/or additional ingredients described herein.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the formulator and safety considerations for the final product.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked polyvinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxy ethylene sorbitan [Tween 60], polyoxy ethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, polyvinylpyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, camauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

In certain preferred embodiments, the particles can be formulated with one or more naturally occurring oils. In such cases, total removal of the oil from the final particle product may not be required. Such oils include animal derived oils, plant derived oils, and algae derived oils, e.g. almond oil, avocado seed oil, cocoa butter, coconut oil, corn oil cottonseed oil, flax seed oil, grapeseed oil, hemp oil, olive oil, palm kernel oil, peanut oil, pumpkin seed oil, rice bran oil, safflower oil, sesame seed oil, sunflower seed oil, soybean oil, walnut oil, Almond oil, Beech nut oil, Brazil nut oil, Cashew oil, Hazelnut oil, Macadamia oil, Mongongo nut oil (or manketti oil), Pecan oil, Pine nut oil, Pistachio oil, Bitter gourd oil, Bottle gourd oil, Buffalo gourd oil, Butternut squash seed oil, Egusi seed oil, pumpkin seed oil, watermelon seed oil, acaf oil, black seed oil, blackcurrant seed oil, borage seed oil, evening primrose oil, flaxseed oil, Amaranth oil, apricot oil, apple seed oil, Argan oil, avocado oil, Babassu oil, Ben oil, Borneo tallow nut oil, Cape chestnut oil, carob pod oil (Algaroba oil), cocoa butter, cocklebur oil, Cohune oil, coriander seed oil, date seed oil, Dika oil, false flax oil, grape seed oil, hemp oil, kapok seed oil, Kenaf seed oil, Lallemantia oil, Mafura oil, meadowfoam seed oil, mustard oil, *Niger* seed oil, poppy seed oil, nutmeg oil, okra seed oil, *papaya* seed oil, *Perilla* seed oil, persimmon seed oil, Pequi oil, Pili nut oil, pomegranate seed oil, pracaxi oil, virgin pracaxi oil, prune kernel oil, *quinoa* oil, Ramtil oil, Royle oil, Sacha inchi oil, Sapote oil, Seje oil, Taramira oil, tea seed oil (*Camellia* oil), thistle oil, tigernut oil (or nut-sedge oil), tobacco seed oil, tomato seed oil, wheat germ oil, castor oil, coconut oil, Colza oil, Corn oil, false flax oil, palm oil, radish oil, rapeseed oil, Ramtil oil, safflower oil, Salicornia oil, soybean oil, sunflower oil, Tung oil, Copaiba oil, Jatropha oil, jojoba oil, Nahor oil, paradise oil (seeds of Simarouba *glauca*,), petroleum nut oil, Pongamia oil, Amur cork tree fruit oil, Astrocaryum murumuru butter oil, Balanos oil, bladderpod oil, Bmcea *javanica* oil, burdock oil (Bur oil) Buriti oil, candlenut oil (Kukui nut oil), carrot seed oil, castor oil, Chaulmoogra oil, *Crambe* oil, Croton oil (tiglium oil), *Cuphea* oil, honesty oil (seeds of Lunaria *annua*), Illipe butter, jojoba oil, mango oil, Mowrah butter oil, Neem oil, Ojon oil, *Passiflora edulis* passion fruit oil, rose hip seed oil, rubber seed oil, sea buckthorn oil, sea rocket seed oil, Snowball seed oil (*Viburnum* oil), Tall oil, Tamanu or foraha oil, Tonka bean oil (Cumaru oil), Tucuma butter oil, or Ucuhuba seed oil.

Liquid dosage forms for oral and parenteral administration include, but are not limited to, pharmaceutically acceptable emulsions, microemulsions, solutions, suspensions, symps and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and perfuming agents. In certain embodiments for parenteral administration, conjugates can be mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions, may be formulated according to the known art using suitable dispersing or wetting agents and suspending agents. The sterile injectable preparation may be a sterile injectable solution, suspension or emulsion in a nontoxic parenterally acceptable diluent. Among the acceptable vehicles, that may be employed are water, Ringer's solution, U. S. P. and isotonic sodium chloride solution, etc. In addition, sterile, fixed oils are conventionally employed as a suspending medium. For this purpose any bland fixed oil can be employed including synthetic mono- or diglycerides. In addition, fatty acids such as oleic acid are used in the preparation of injectables.

In order to prolong the effect of an active ingredient, it is often desirable to slow the absorption of the active ingredient from subcutaneous or intramuscular injection. This may be accomplished by the suspension of the particles into a liquid with poor water solubility. The rate of absorption of the active ingredient then depends upon the rate of the dispersion of the liquid and the release of the particles, which, in turn, may depend upon particle size and form. In some embodiments, delayed release of the particles is accomplished by suspension in an oil vehicle.

Compositions for rectal or vaginal administration are typically suppositories which can be prepared by mixing the conjugates with suitable non-irritating excipients such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the particles may be added neat or mixed with at least one inert, pharmaceutically acceptable excipient such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

Spray or aerosol formulations may include one or more propellants. Low boiling propellants generally include liquid propellants having a boiling point of below 65° F. at atmospheric pressure. Generally the propellant may constitute 50 to 99.9% (w/w) of the composition, and the particles may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide the active ingredient in the form of droplets of a particle suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 µm to about 200 µm.

Disclosed herein are methods for preparing the particles disclosed above. Generally speaking, the particles can be prepared by applying a shear force to a composition of water and fibrin. The fibrin may be obtained by combining fibrinogen with thrombin. This material may be designated thrombin-polymerized fibrin. Generally, no exogenous Factor XIII or non-biological crosslinking agent (e.g., glutaraldehyde) is be added to the fibrinogen/thrombin mixture.

Shear force may be applied to the composition using a variety of techniques, including spraying, for instance spray drying or electrospray, or by injecting the aqueous composition into a water-immiscible fluid into as in a bulk reactor. In such mixing processes, the aqueous composition may be termed the dispersive phase, and the water-immiscible fluid is termed the continuous phase. Generally, the continuous phase will have a viscosity that is different from the viscosity of the aqueous phase, for instance either greater or lower, preferably the continuous phase has a greater viscosity than the dispersive phase. Suitable fluids for the continuous phase include oils, e.g., plant, animal, or algae derived oils as described above. In each case, it is preferred that the shear force is applied at a temperature no greater than 40° C., no greater than 25° C., no greater than 20° C., no greater than 15° C., no greater than 10° C., or no greater than 4° C. In some cases, the shear force can be applied at a temperature between 4-40° C., between 10-40° C., or between 10-25° C.

In a preferred embodiment, the shear force can be applied using a microfluidic device capable of combining two or more fluid streams (at an incident angle that can range between 0-π). Importantly, the fluid in the continuous phase must be immiscible with the fluid in the dispersive phase. The dispersive phase includes water and a polymerized fibrin, which can be obtained by combining fibrinogen and thrombin. Generally, the dispersive phase does not include externally added factor XIII or non-biologically derived agents capable of crosslinking the fibrin molecules.

In a preferred embodiment, the continuous phase stream is passed through a continuous channel, and the dispersive phase stream is passed through at least one dispersive channel. The fluid from the dispersive channel is injected into the flowing continuous phase stream. As used herein, the term "channel" refers to a feature on or in an device (substrate) that at least partially directs the flow of the fluid contained there within. The channels are not particularly limited in their shape, and the shape of the channel can be defined by the shape of an imaginary cross-section taken perpendicular to the flow of fluid through the channel. By way of example, a perfectly cylindrical channel will have a circular cross-section. Other suitable cross-sections include ovals, squares, rectangles, triangles, pentagons, and hexagons.

In some embodiments, the continuous channel can be cylindrically shaped, having a perpendicular circular cross-section having a diameter no greater than about 1,000 µm, no greater than about 750 µm, no greater than about 500 µm, no greater than about 250 µm, no greater than about 100 µm, no greater than about 50 µm, or no greater than about 10 µm. The dispersive channel can be a cylinder, having a perpendicular circular cross-section having diameter no greater than about 1,000 µm, no greater than about 750 µm, no greater than about 500 µm, no greater than about 250 µm, no greater than about 100 µm, no greater than about 50 µm, or no greater than about 10 µm.

The size of the channel can be defined by the area of an imaginary cross-section taken perpendicular to the flow the fluid in the channel, designated herein the cross-sectional area. For instance, the cross section for the dispersive channel can be no greater than $10^3$ µm$^2$, no greater than $10^4$ µm$^2$, no greater than $10^3$ µm$^2$, or no greater than $10^2$ µm$^2$. In some embodiments, the cross-sectional area of the continuous channel can be no greater than $10^5$ µm$^2$, no greater than $10^4$ µm$^2$, no greater than $10^3$ µm$^2$, or no greater than $10^2$ µm$^2$.

In certain embodiments, the continuous channel will be approximately the same size as the dispersive channel. In other embodiments, the continuous channel will be larger than the dispersive channel.

The dispersive channel is in fluid communication with the continuous channel. At the point where the channels are joined, the dispersive phase is introduced into the continuous phase, thereby forming droplets and creating a shear force sufficient to convert the bulk fibrin into fibrin particles. The dispersive channel may be disposed at any angle relative to the flow of fluid in the continuous channel. In some embodiments, the dispersive channel may be disposed at a 90° angle relative to the continuous channel. In other embodiment, the dispersive channel may be disposed at an angle less than 90° relative to the continuous channel, as shown in FIG. 1. For instance, the dispersive channel may be disposed, relative to the continuous channel, at an angle from 1-90°, from 5-85°, from 10-75°, from 15-60°, from 45-60°, from 10-30°, from 30-45°, from 45-60°, from 60-75°, or from 75-90°. In some embodiments, the dispersive channel may be disposed, relative to the continuous channel, at an angle from 90-179°, from 95-175°, from 100-165°, from 105-150°, from 135-150°, from 100-120°, from 120-135°, from 135-150°, from 150-165°, or from 165-180°. Multiple dispersive channels can be introduced into a single continuous channel. The particles are formed at the intersection of the dispersive and continuous channels and pass down the continuous channel to be collected at an outlet. The particles can be separated from the continuous phase, and may be buffer exchanged into a suitable aqueous vehicle, and optionally frozen or lyophilized.

Either of the continuous or dispersive streams can include additional agents, such as one or more therapeutic agents, surfactants, antioxidants, hydrogels, thickeners, etc.

The fluids moving through each of the first and second streams will experience varying degrees of shear, depending on the flow rate of the liquid, the viscosity of the liquid, and the geometry of the microfluidic device channels. The relative fluid velocity between the first and second streams can be controlled, and in certain instances the relative fluid velocity between the continuous phase and dispersive phase can be from at least about 1:1, at least about 2:1, at least about 5:1, at least about 10:1, at least about 20:1, or at least about 50:1. As used herein, at least 2:1 includes all ratio in which the first component is 2 or greater, i.e., 3:1, 5:1, 20:1, etc.

An advantage of the processes disclosed herein is that the particles can be prepared without an external heat stimulus. For instance, the fibrin polymerization and the particle formation can be conducted at a temperature no greater than 40° C., no greater than 25° C., no greater than 20° C., no greater than 15° C., or no greater than 4° C. The skilled person will of course recognize that the particles will be prepared at a temperature in which both the continuous and dispersive phases will flow through the microchannels.

The dispersive and/or continuous phase may also include one or more therapeutic agents, such as described above, hi certain embodiments, the therapeutic agent will be encapsulated by the fibrin as the particle is formed. This can be achieved by including the therapeutic agent in the dispersive phase. The therapeutic agent may be freely combined with water, fibrinogen, and thrombin (along with any other desired components). In other embodiments, the therapeutic agent may be conjugated to fibrinogen prior to treatment with thrombin, or may be conjugated to the polymerized fibrin prior to shearing into particles.

In other embodiments, the therapeutic agent may be combined with the particles subsequent to particle formation. In some cases, lyophilized particles may be reconstituted with a solution containing the therapeutic agent to trap the agent within the rehydrated particles or to promote adsorption throughout the particles. The therapeutic agent may also be adsorbed to or conjugated to the as-formed particles using the conjugation techniques described above. Combinations of the above methods may also be employed. For instance, the particles can be reconstituted with a solution containing a first therapeutic agent (for instance an antibiotic), and covalently conjugated to a second therapeutic agent (for instance a targeting factor). The agents can be added in any order that best preserves the activity of the therapeutic agents and promotes optimum trapping or attachment of the agents.

EXAMPLES

The following examples are for the purpose of illustration of the invention only and are not intended to limit the scope of the present invention in any manner whatsoever.

Example 1—Fabrication and Characterization of Fibrin Nanoparticles (FBN)

One method of creating the fibrin nanoparticles is to use a microfluidic device configured to generate droplets of one fluid in another immiscible fluid to shear a polymerized fibrin gel into small particles.

Figure 2:
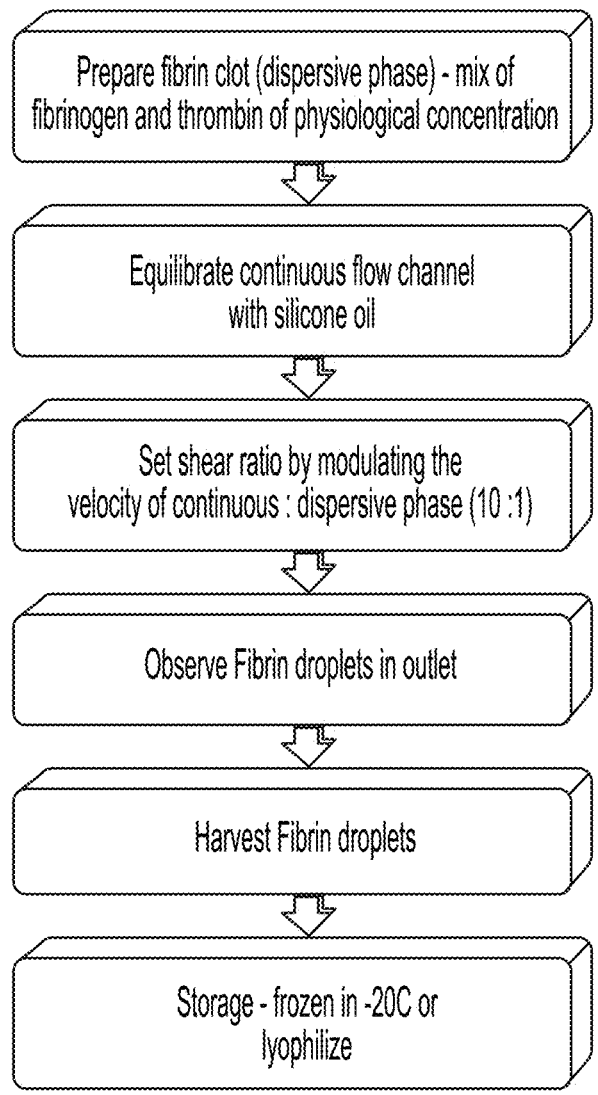
FIG. 2 includes a schematic of an exemplary process to prepare nanoparticles.

Human fibrinogen (1 mg/ml; depleted of plasminogen, von Willebrand factor and fibronectin, FIB3, Enzyme Research Laboratories, South Bend, Ind.) was reacted with 0.5 U/ml human a thrombin (HT 1002a, Enzyme Research Laboratories, South Bend, Ind.) in HEPES buffer (25 mM HEPES, 150 mM NaCl, 5 mM CaCl$_2$) pH 7.4 to generate fibrin. The reaction was carried out within a syringe and the syringe connected to the inlet of the dispersive channel in the microfluidic droplet generator (FIG. 1). The microfluidic channels of the droplet generator were made from laser cut 3M tape (100 µm wide dispersive channel, 250 µm wide continuous channel, height of ~400 µm) sandwiched between acrylic and glass sheets. The fibrin reaction product was sheared into tiny droplets by introducing it through the dispersive channel into the continuous channel containing an immiscible stream of synthetic oil. The nanoparticles were harvested by centrifugation at 10,000 G for 2 hours to remove silicone oil (FIG. 2). Modulating the flow velocities of continuous and dispersive fluids controlled the droplet size and consequently the nanoparticle size. The dialysis and or washing steps were performed in water in cases where the nanoparticles were to be subsequently lyophilized. During either the rehydration or a final washing step, the nanoparticles were resuspended in HEPES buffer.

The size and 3D globular structure of the hydrated fibrin nanoparticles were characterized using dynamic light scattering (DLS) and cryogenic scanning electron microscopy (Cryo-SEM). The particle volume and surface charge of the fibrin nanoparticles was measured in a Zetasizer (Malvern, UK) and globular 3D structure was visualized after freezing the particles in HEPES buffer and following Cryo-SEM sample preparation protocols. For atomic force microscopy (AFM) analysis of dehydrated fibrin nanoparticles, glass cover slips were dipped and cleaned in a series of solutions from detergent (Alconox), distilled water, acetone, absolute ethanol and isopropanol. The cleaned glass cover slips were pretreated with 3-aminopropyltrimethoxysilane (Sigma Aldrich, Mo. USA) washed and incubated with fibrin nanoparticles (1 mg/ml) while shaking at room temperature for 15 min. The cover slips were spun in a centrifuge and air-dried in a fume hood. The air-dried FBN were characterized using AFM (Asylum Research, Santa Barbara, Calif.) using AFM probes obtained from NanoAndMore USA (Watsonville, Calif.) and operated in air topography mode. The diameter and height trace of each air-dried particle were captured in Igor Pro and analyzed using ImageJ.

Keratinocyte growth factor (CYT-219, Prospec Protein Specialist, East Brunswick N.J.) was covalently coupled to FBN using 1-ethyl-3-(3-dimethylaminopropyl) carbodiimide and N-hydroxysulfosuccinimide, (CAS 25952-53-8 and CAS 106627-54-7, ThermoFisher Scientific, Waltham Mass.) under standard conditions (Hermanson GT, 2013).

Figure 3:
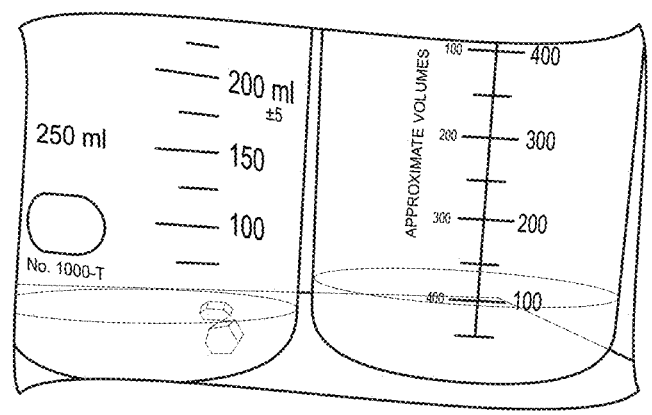
FIG. 3 includes a depiction of harvested nanoparticles in oil compared to products from mixing fibrinogen with inactive thrombin (control, nonpolymerized starting material).
Figure 4:
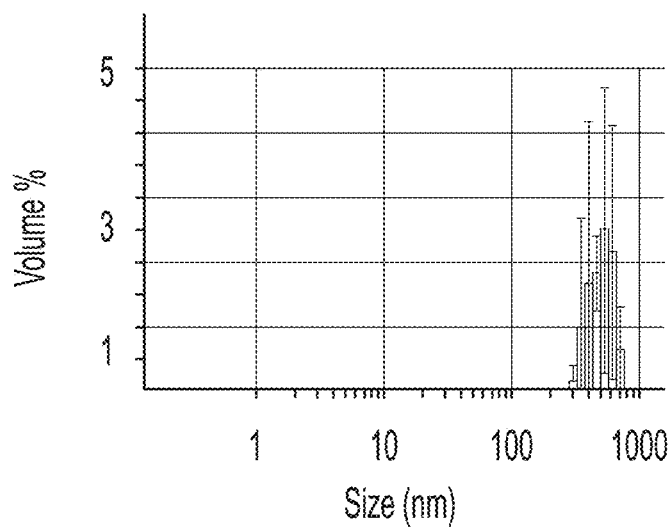
FIG. 4 includes a depiction of % volume of nanoparticles (y-axis) and particle size (x-axis).
Figure 5:
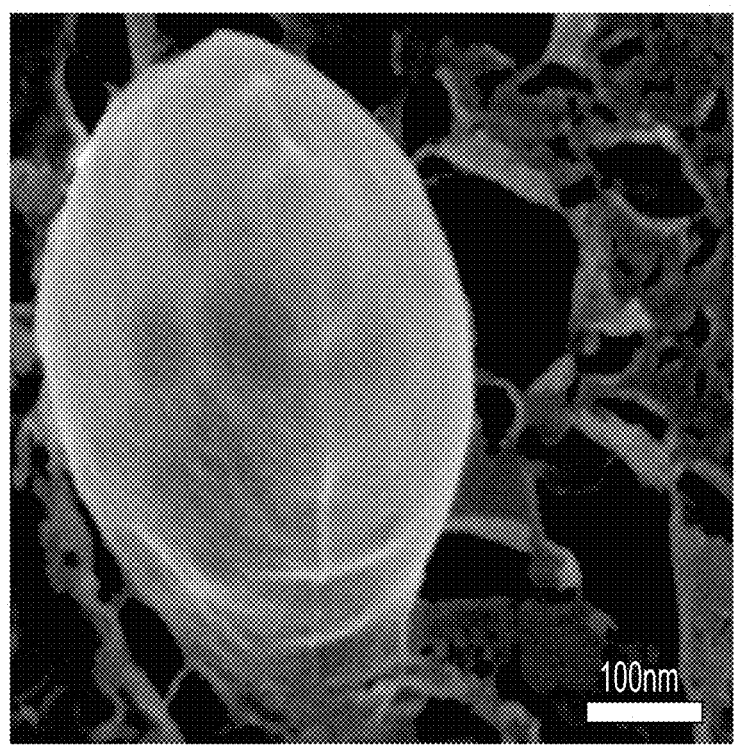
FIG. 5 includes a cryogenic scanning electron micrograph of a fibrin nanoparticle.
Figure 6:
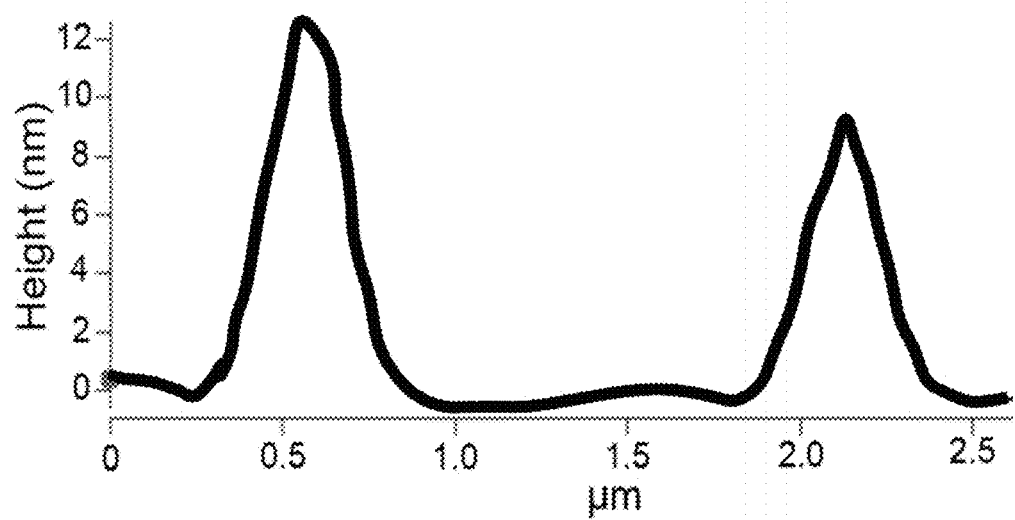
FIG. 6 include an atomic force microscope (AFM) topographic trace of air dried nanoparticles. The dried particles are 500 nm in diameter and 8-10 nm in height.

After shearing in the droplet generator, the fibrin particles (FBN) collected at the exit from the continuous channel appeared as cloudy suspension at room temperature (FIG. 3). Washing to remove residual oil produced a clear suspension of FBN. The purified FBN were resuspended in HEPES buffer pH 7.4 to the 2 mL initial gel volume and stored at −20° C. No aggregates were observed under these conditions. The average volumetric diameter of hydrated fibrin nanoparticles in this preparation was measured to be 600±200 nm in DLS (FIG. 4) and the shapes ranged from circular to oblong (FIG. 5). Air-dried FBN were characterized using AFM (air topography mode); the dehydrated FBN exhibited a spread and flat structure with a diameter of 370±235 nm and a height of 15±14 nm (n=60, representative FIG. 6).

Example 2—FBN and FBN-KGF to Expedite Cell Recruitment

One potential advantage of FBN over bulk fibrin wound treatments is the ability to support cell migration into the wound to expedite healing. As a model for the impact of this activity on FBN, we used an in vitro model of a human wound. Keratinocyte growth factor (KGF) is a well-known growth factor involved in tissue healing. KGF is of mesenchymal origin and enhances the regenerative capacity of epithelial tissues. In addition, we tested the possibility that administering FBN carrying KGF to wound site would enhance the rate of the cellular re-epithelialization and wound healing compared to FBNs alone.

Human dermal fibroblasts (500,000 cells/ml) were embedded in 3D collagen gels (3 mg/ml) in serum-free culture media. Using biopsy punches, "wounds" 2 mm in diameter were created with approximately 0.5-1 mm depth. The biopsied 3D wounds were filled with fibrin nanoparticles (FBN), FBN with attached Keratinocyte Growth Factor (FBN-KGF) or saline (controls). The number of cells migrating into the hole from the surrounding 3D collagen gel was counted every 18-24 hours. Data from each sample was normalized to its biopsy area (in $mm^2$). The cell migration rate was measured by counting cell numbers within the normalized biopsy area (# cells/unit area) on each day. Each treatment was compared with saline and KGF only controls.

KGF was covalently attached to preformed FBN and administered to in vitro 3D wounds by adding 20 (μl of sample into the biopsied region of the collagen matrix. FBN, when functionalized with KGF, showed significantly enhanced cell recruitment and or cell proliferation in 3D collagen gels compared with saline and free KGF controls. FBN alone was not sufficient to enhance cell migration. It appears that a chemotactic agent is required in order to induce cell migration into the wound bed. However, we do show that FBNs do not inhibit cell migration as bulk fibrin sealants have previously been reported to do (references below). Bulk fibrin sealants require high concentrations of fibrinogen and thrombin in order to induce fast polymerization at the surgical/wound site; by delivering prepolymerized FBNs we are able to circumvent this issue and without inhibiting migration.

REFERENCES

(26) Hanson, A. J.; Quinn, M. T. Effect of Fibrin Sealant Composition on Human Neutrophil Chemotaxis. J. Biomed. Mater. Res. 2002, 61 (3), 474-481.
(27) Brittberg, M.; Sjögren-Jansson, E.; Lindahl, A.; Peterson, L. Influence of Fibrin Sealant (Tisseel) on Osteochondral Defect Repair in the Rabbit Knee. Biomaterials 1997, 18 (3), 235-242.
(28) Lanir, N.; Ciano, P. S.; Van de Water, L.; McDonagh, J.; Dvorak, A. M.; Dvorak, H. F. Macrophage Migration in Fibrin Gel Matrices. II. Effects of Clotting Factor XIII, Fibronectin, and Glycosaminoglycan Content on Cell Migration. J. Immunol. 1988, 140 (7), 2340-2349.
(29) Yeung, A. M.; Faraj, L. A.; McIntosh, O. D.; Dhillon, V. K.; Dua, H. S. Fibrin Glue Inhibits Migration of Ocular Surface Epithelial Cells. Eye 2016, 30 (10), 1389-1394.

Example 3—Cell Adhesion to FBN

The traction force a single cell exerts on its substrate is an indirect indicator of its intracellular contractility. Measuring the basal traction stresses of single cells on a functionalized polyacrylamide substrate provided an indirect comparison of the effect of the FBN on dermal fibroblast contractility and the ability of the cells to exert forces on the substrate. Human dermal fibroblast contractility on different functionalized substrates (FBN, collagen and bulk fibrin) was compared.

The interaction (adhesive traction) of human dermal fibroblasts with fibrin nanoparticles was quantified using Traction Force Microscopy (TFM). Fibrin nanoparticles, bulk fibrin or collagen peptides were immobilized onto 8.8 kPa polyacrylamide hydrogels pretreated with sulfosuccinimidyl 6-(4'-azido-2'-nitrophenylamino)hexanoate (sulfo-SANPAH) (Tse and Engler, 2010). The fluorescent microspheres (300 nm average diameter, Spherotek) embedded in the hydrogel provided fiduciary markers for traction measurements. The FBN, bulk fibrin or collagen was immobilized after overnight incubation at 4° C., the substrates were rinsed twice with phosphate buffered saline (PBS), and sterilized by irradiation (365 nm) for at least 15 min, before seeding cells. Human fibroblasts were seeded at 10,000 cells/ml onto 8 mm diameter hydrogels, and allowed to adhere and spread for a maximum of 5 hr at 37° C. under 5% $CO_2$. Under 20× magnification, 1.5× NA, (EVOS fluorescent microscope), the fluorescent image of the bead positions was marked before and after cell detachment (3% SDS in PBS treatment). The absolute basal route mean square (RMS) traction force (BTF) was determined from fiduciary bead displacements, relative to the traction-free bead positions after cell removal (Butler et al., 2002) using MATLAB. Constrained traction maps and the RMS traction stress (Pa; $N/m^2$) were determined from the bead displacement maps and compared. The means and standard error of the means were statistically computed in Microsoft Excel and significance compared using Student's 2-tailed t-test.

Figure 7:
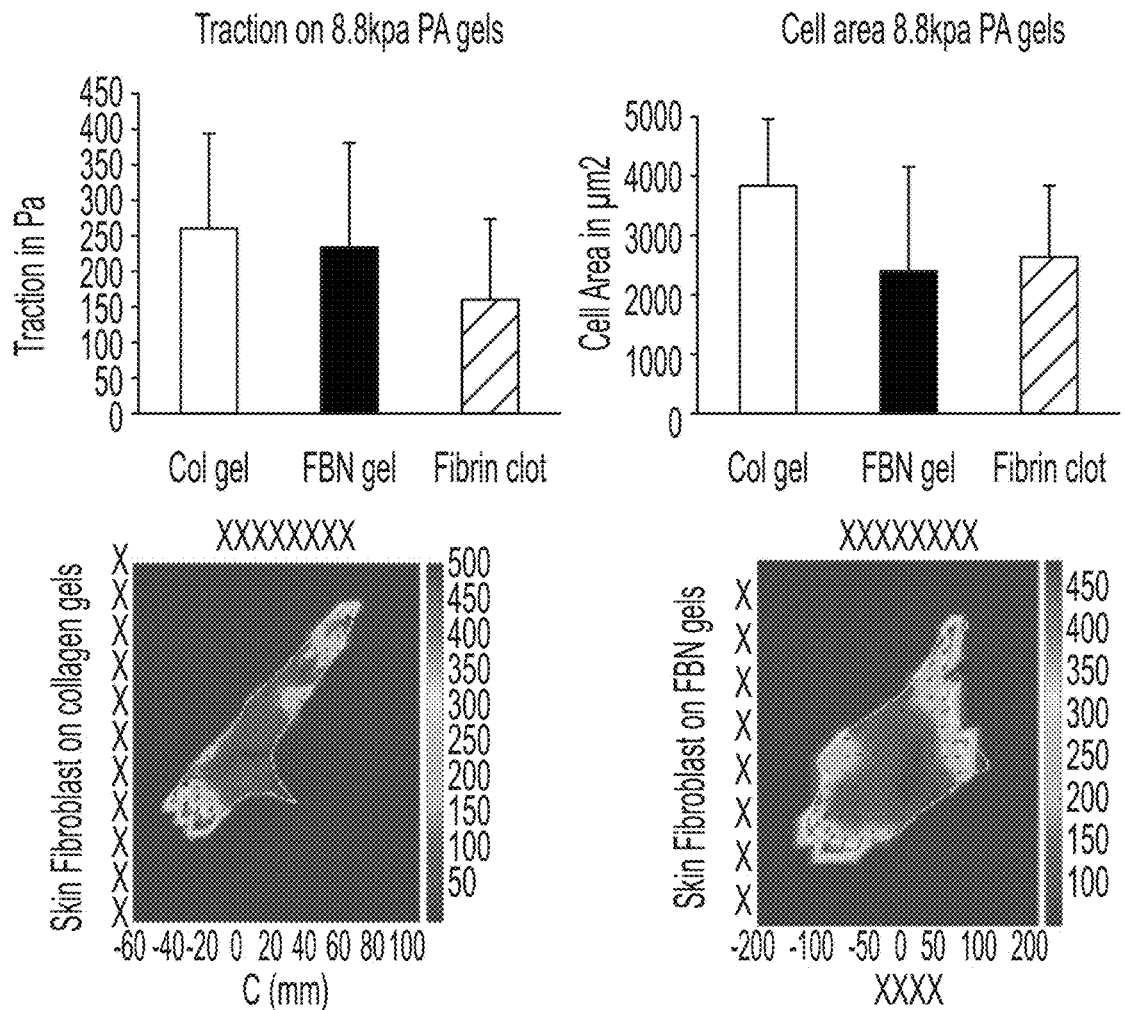
FIG. 7 includes a comparison of traction force generated by individual cells adherent to a layer of nanoparticles compared cells adherent to bulk fibrin gels.
Figure 8:
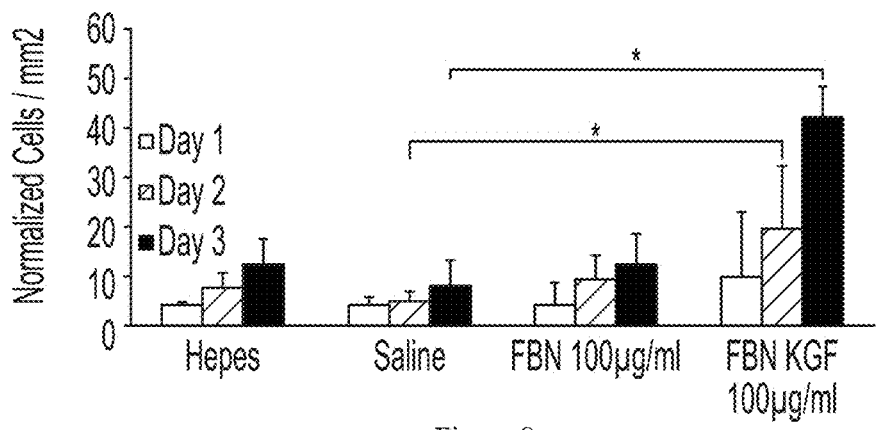
FIG. 8 includes a depiction of cell recruitment enhanced by keratinocyte growth factor (KGF) coupled nanoparticles compared to a saline control or nanoparticles without KGF.

Cells on FBN-coated surfaces produced a traction force of 233±150 Pa (n=11), while on collagen and bulk fibrin gels, the cells produced 260±133 Pa (n=23) and 165±105 Pa (n=5), respectively (FIG. 7). The data were not significantly different from one other, suggesting that dermal fibroblasts were adhering just as well onto FBN as they do to collagen or bulk fibrin gels. This indicates that fabrication of fibrin into FBNs does not hinder the ability of cells to interact with the cell adhesive regions of fibrin.

Example 4—Animal Studies

In vivo validation that fibrin nanoparticles can assist wound healing was performed in mice. Dermal wounds were created and the rate of healing measured over several days.

Two epithelial dorsal dermal wounds were created in 10-week-old healthy male C57BF/6 mice (Charles River Faboratories Wilmington, Mass.) using a 4 mm diameter biopsy punch. The skin was excised and the inner endometrial lining was removed using surgical tools. Wound healing due to skin refolding was prevented by stitching the surrounding skin to a sterilized silicone ring. The annular silicone ring was laser cut from a silicone sheet acquired from Grace Bio-Fabs, Bend, Oreg., to a required inner diameter of 4.9 mm. The silicone ring was held in position with stationary glue and stitches. The glue did not touch the wound, but was in contact with remote edges of the silicone ring and outer skin.

Figure 9:
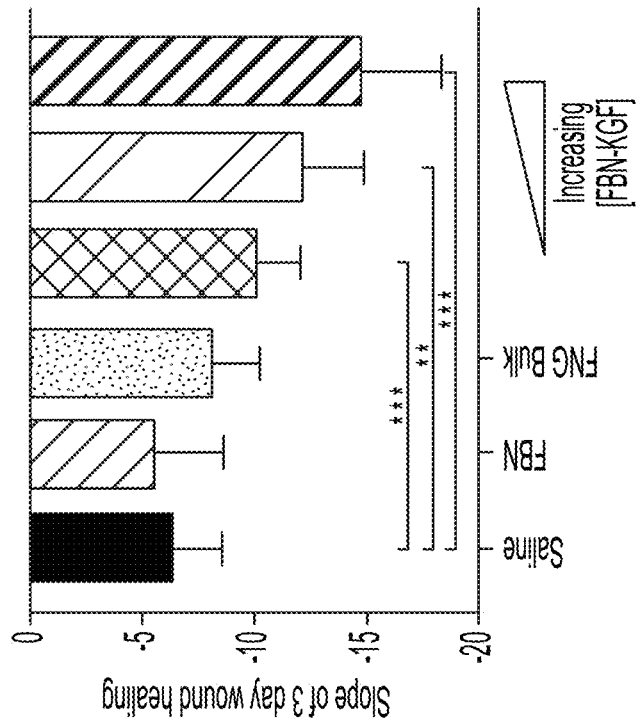
FIG. 9 includes a depiction of in vivo enhancement of wound healing by KGF coupled nanoparticles compared to a saline control or nanoparticles without KGF.
Figure 9:
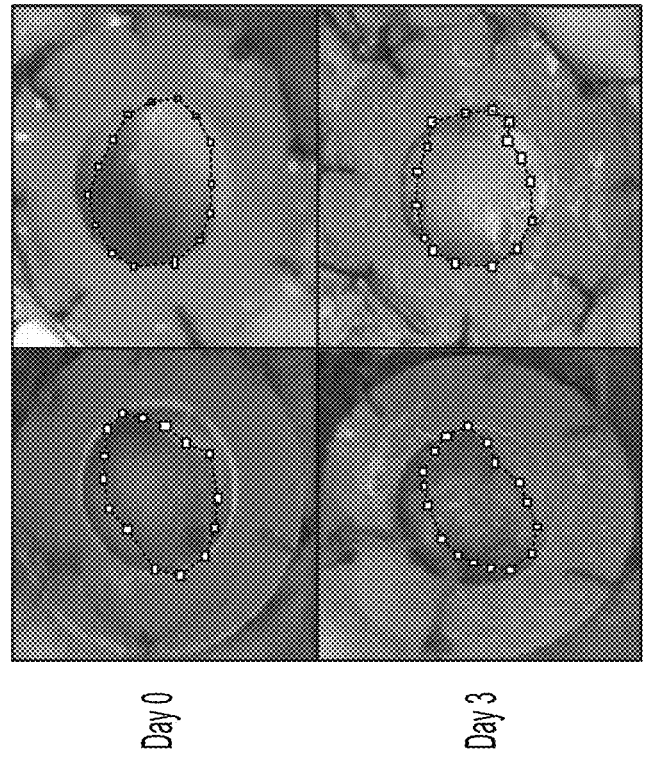
Figure 10:
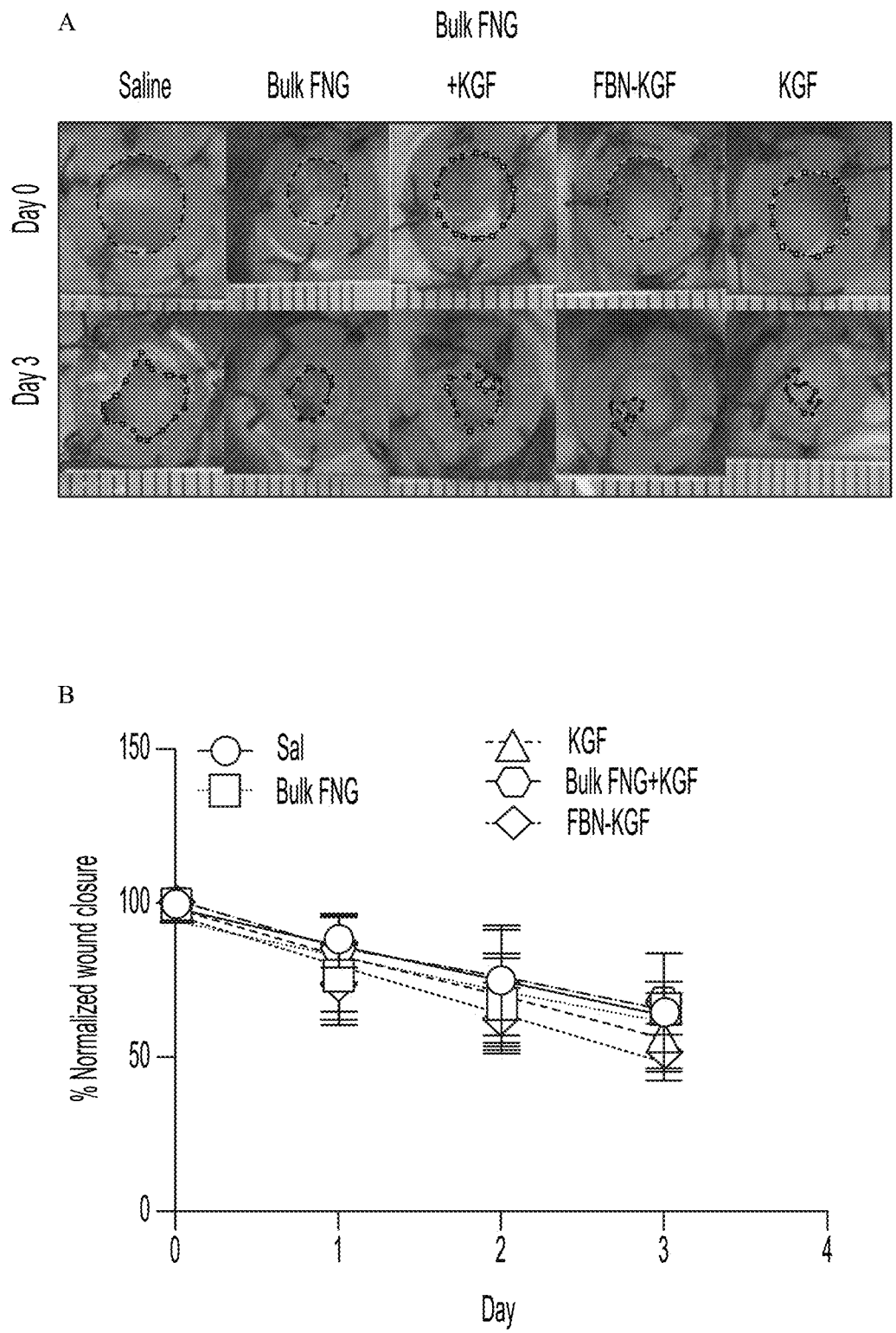
FIG. 10 include a depiction of in vivo enhancement of wound healing by saline control, bulk nanoparticles, KGF, bulk nanoparticles admixed with KGF, and KGF coupled-nanoparticles.

Each wound was immediately imaged using a handheld Nikon camera and separately treated with control 0.9% saline, bulk fibrin gel (400 (μg), FBN (20 (μg), or FBN-KGF (20 μg at the highest concentration). After treatment, the wound was covered with translucent moisture responsive catheter dressing (IV3000, Smith & Nephew, Andover, Mass.) attached over the silicone ring. The porous sheet was also laser cut to the required dimensions to aid the surgeon and to match the wound area. The wound area was imaged using a handheld Nikon camera every 24 hours after removing the translucent dressing. Image analysis of the wound was performed in ImageJ and the scale was measured using the known inner diameter of the silicone ring. The % change in wound area on each day was compared its wound area in day 0 (day of biopsy). The rate of wound healing was quantified by plotting averaged % normalized wound area for each wound treatment. The slope of a linear fit of the average % normalized wound area for the first 3 days post biopsy was calculated in Prism and 2-way Anova statistics were performed to compare the slopes of each treatment (FIG. 9).

FBN-KGF closed dermal wounds with a 3-day average dermal area closure of 48±9% (n=7), compared to saline (n=7, 35±19%), bulk fibrin (n=6, 34±9%), bulk fibrin mixed (n=7, 35±19%), or free KGF (10 μmol, n=9, 42±12%). Assuming a linear healing rate of the first 3 days, the slopes of FBN-KGF was −16±3, compared with saline (−12±0.3), bulk fibrin (−11±3), bulk fibrin mixed with KGF (−11±2) and free KGF (−14±2). These results indicate that delivery of KGF via FBN enhances wound healing outcomes to a greater degree than delivery of free KGF alone or delivery via bulk fibrin gels.

Example 4—Entrapment of Therapeutic Agents into Nanoparticles

Infection can be a major factor in the rate at which wounds heal. FBN can be used to deliver antimicrobial agents to wounds as another mechanism to expedite wound healing.

In vitro biofilms of the bacteria *Staphylococcus* were generated in a 6-well tissue culture plate using *S. aureus* strain in specific growth media. The culture volumes were optimized for drug dosage and concentration. Lyophilized fibrin nanoparticles (2 mg) were combined with either (a) doxycycline (1 mg); (b) LL37 (LL37 is a cathelicidin family 37 amino acid long antimicrobial peptide expressed in certain human epithelial cells) (20 ug); or (c) doxycycline (1 mg)+LL37 (20 ug).

The samples were centrifuged once at 14000 rpm for 15 minutes to remove antibiotic not trapped in the FBN, and the supernatant removed. The fibrin nanoparticles pellets were then lyophilized and tested for the ability to inhibit the growth of *S. aureus*. The fibrin nanoparticles, with and without entrapped antibiotics, were suspended in 200 μl HEPES buffer and mixed with pre-grown *S. aureus* biofilms for a 24-hour period.

Inhibition of *S. aureus* growth with LL37 alone (20 jag), doxycycline (1 mg), FBN+doxycycline (1 mg), FBN+LL37 (20 jag), FBN+doxycycline (1 mg)+LL37 (20 jag) was separately investigated and compared by plotting colony forming units (in log scale) from each treatment and the untreated control. FBN containing doxycycline exhibited the strongest inhibitory effect on *S. aureus* growth; this inhibition was greater than that observed in the presence of free doxycycline.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

REFERENCES CITED

Butler, James P, Iva Marija Tolić-Nørrelykke, Ben Fabry, and Jeffrey J Fredberg. 2002. "Traction Fields, Moments, and Strain Energy That Cells Exert on Their Surroundings." *American Journal of Physiology. Cell Physiology* 282 (3): C595-605. doi: 10.1152/ajpcell.00270.2001.

Seemann, Ralf, Martin Brinkmann, Thomas Pfohl, and Stephan Herminghaus. 2012. "Droplet Based Microfluidics." *Reports on Progress in Physics* 75 (1). IOP Publishing: 16601. doi: 10.1088/0034-4885/75/1/016601.

Takeichi, M, and S Nakagawa. 2001. "Cadherin-Dependent Cell-Cell Adhesion." *Current Protocols in Cell Biology/Editorial Board*, Juan S. Bonifacino . . . [et Al.] Chapter 9 (May): Unit 9.3. doi: 10.1002/0471143030.cb0903s00.

Tse, Justin R, and Adam J Engler. 2010. "Preparation of Hydrogel Substrates with Tunable Mechanical Properties." *Current Protocols in Cell Biology/Editorial Board*, Juan S. Bonifacino . . . [et Al.] Chapter 10 (June): Unit 10.16. doi:10.1002/0471143030.cb1016s47.

Wang, Ning, Iva Marija Tolić-Nørrelykke, Jianxin Chen, Srboljub M Mijailovich, James P Butler, Jeffrey J Fredberg, and Dimitrije Stamenović. 2002. "Cell Prestress. I. Stiffness and Prestress Are Closely Associated in Adherent Contractile Cells." *American Journal of Physiology. Cell Physiology* 282 (3): C606-16. doi: 10.1152/ajpcell.00269.2001.

What is claimed is:

1. A plurality of particles, comprising thrombin-polymerized fibrin, wherein the particles have an average particle size between 100-10,000 nm, in the hydrated state, wherein the thrombin-polymerized fibrin is not denatured, wherein the particles are less than 15% crosslinked.

2. The particles according to claim 1, wherein the particles are less than 5% crosslinked.

3. The particles according to claim 1, comprising at least one therapeutic agent wherein the at least one therapeutic agent is dispersed throughout the particle, attached to the surface of the particle, or both.

4. The particles according to claim 1, comprising at least one therapeutic agent covalently conjugated to the particle.

5. The particles according to claim 4, wherein the at least one therapeutic agent comprises at least one antibacterial agent.

6. The particles according to claim 1, comprising at least one growth factor, at least one cell recruiting factor, or a combination thereof.

7. A pharmaceutical composition, comprising the particles of claim 1, and one or more pharmaceutically acceptable excipients.

8. A method of treating a wound in a patient in need thereof, comprising administering to the patient the composition of claim 7.

9. The method according to claim 8, wherein the composition is directly applied to the wound area.

10. The method according to claim 8, wherein the composition is administered to the patient orally, transdermally, parenterally, by inhalation, intraocularly, or by suppository.

11. The method according claim 8, wherein the wound comprises a trauma wound, a surgical wound, a burn wound, or an ulcer wound.

12. The method according to claim 8, wherein the patient in undergoing anti-coagulation therapy.

13. The method according to claim 8, wherein the particles in the composition comprise at least one antibiotic in an amount effective to treat or prevent infection at the wound site.

* * * * *